(12) United States Patent
Grinberg

(10) Patent No.: US 7,172,561 B2
(45) Date of Patent: Feb. 6, 2007

(54) SPREADER TENSIOMETER FOR MEASURING TENSION IN AN INTERVERTEBRAL DISC SPACE

(75) Inventor: Alexander Grinberg, Newton, MA (US)

(73) Assignee: Depuy Acromed, Raynham, MA (US)

( * ) Notice: Subject to any disclaimer, the term of this patent is extended or adjusted under 35 U.S.C. 154(b) by 530 days.

(21) Appl. No.: 10/247,865

(22) Filed: Sep. 20, 2002

(65) Prior Publication Data
US 2004/0059262 A1    Mar. 25, 2004

(51) Int. Cl.
*A61B 5/103* (2006.01)
(52) U.S. Cl. .................. 600/587; 600/594; 606/105
(58) Field of Classification Search ............. 600/587, 600/594; 606/105, 205, 206, 207, 209; 81/477, 81/862.21, 467, 478, 480; 73/862.21, 862.08; 33/501.04, 511, 512, 513
See application file for complete search history.

(56) References Cited

U.S. PATENT DOCUMENTS

| | | | |
|---|---|---|---|
| 2,394,022 A * | 2/1946 | Storrie ................... 73/862.21 |
| 4,066,082 A | 1/1978 | Arcan et al. |
| 4,271,836 A | 6/1981 | Bacal et al. |
| 4,501,266 A | 2/1985 | McDaniel |
| 4,899,761 A | 2/1990 | Brown et al. |
| 5,048,381 A * | 9/1991 | Allen et al. ................... 81/477 |
| 5,213,112 A | 5/1993 | Niwa et al. |
| 5,540,696 A | 7/1996 | Booth, Jr. et al. |
| 5,772,661 A * | 6/1998 | Michelson ................... 606/61 |
| 6,206,922 B1 * | 3/2001 | Zdeblick et al. ......... 623/17.11 |
| 6,325,827 B1 * | 12/2001 | Lin .......................... 623/17.16 |
| 6,575,042 B1 * | 6/2003 | Rinner ......................... 73/847 |
| 2001/0012942 A1 * | 8/2001 | Estes et al. ................. 606/105 |

FOREIGN PATENT DOCUMENTS

FR    2 356 405    1/1978

* cited by examiner

*Primary Examiner*—Max F. Hindenburg
*Assistant Examiner*—Rene Towa
(74) *Attorney, Agent, or Firm*—Thomas M. DiMauro (57) ABSTRACT

The present invention relates to a novel spreader tensiometer adapted for use in measuring tension in an intervertebral disc space.

31 Claims, 8 Drawing Sheets

FIG. 4B

SPREADER TENSIOMETER FOR MEASURING TENSION IN AN INTERVERTEBRAL DISC SPACE

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of bearing weight through a damaged, unstable vertebral joint. One conventional method of managing these problems is to remove the problematic disc and replace it with a prosthetic implant (such as a fusion body, spacer or a motion disk) within the intervertebral disc space.

Generally, intervertebral implant technology relies upon tension provided by natural ligaments adjacent the disc space to keep the implant in place. Accordingly, prior to insertion of the implant, it is typically desirable to measure the degree of tension afforded by these natural ligaments. However, a prevalent manner of measuring intervertebral tension requires the surgeon to insert a distractor into the disc space and manually "feel" the tension so produced. The subjectivity of this method may reduce its reliability.

U.S. Pat. No. 5,213,112 ("Niwa") discloses a tension meter comprising a main body, a fixed arm extending from one end of the main body, and a movable arm disposed parallel to the fixed arm and mounted on the main body so as to be movable away therefrom. In particular, the movable arm has a pair of proximal beams extending normally therefrom that are slidably received in a corresponding pair of throughholes disposed in the main body.

In use, the distal end of each arm is inserted into the disc space, the device is actuated to move the arms apart, and the force required to move the arms apart is measured.

However, since the distal end of the movable arm is subjected to a significant resisting force (from the resisting ligaments), the beam portion of the movable arm may jam in its corresponding hole, thereby reducing the accuracy of the device.

U.S. Pat. No. 4,501,266 ("McDaniel"), U.S. Pat. No. 4,899,761 ("Brown") and U.S. Pat. No. 5,540,696 ("Booth") each disclose a spinal distraction device utilizing a technology similar to Niwa in that the proximal beam portion of their movable arms is disposed in a barrel, and so is subject to the above-discussed jamming.

U.S. Pat. No. 4,066,082 ("Arcan") discloses a device for measuring tension in a disc space, comprising a pivotable device having a load cell fixed to the proximal and distal portions of a single arm and straddling the pivot. As the proximal portion of the device is deflected by stress applied to the jaws, a compressive force is registered in the load cell.

However, since the load cell is disposed about the pivot, the actual change in distance recorded by the load cell is small. Since the reported load is based upon this small change in distance, a small inaccuracy in recorded distance may lead to an inaccurate report of load. Of note, according to Arcan, great accuracy is not required in this technique.

SUMMARY OF THE INVENTION

In an embodiment of the present invention, there is provided a device for measuring tension in an intervertebral disc space in which distraction of the disc space is accomplished by rotation of a spreader, and the force required to achieve the distraction is measured by a torque gauge connected to the spreader.

This embodiment is advantageous over the Niwa-type devices in that the torque produced within the spreader tip can be axially transferred from a proximal handle to a deflection beam housed with the measuring device without any undesirable jamming.

Therefore, in accordance with the present invention, there is provided a tensiometer for measuring tension in an intervertebral disc space between opposed vertebral surfaces, comprising:
 a) a disc spacer spreader adapted to enter a disc space and distract the disc space upon rotation,
 b) a torque gauge adapted to engage the disc space spreader and report a torque required for the rotation of the spreader.

Also in accordance with the present invention, there is provided a method of measuring tension in an intervertebral disc space formed from opposed vertebral endplates, comprising:
a) providing a tensiometer for measuring tension in an intervertebral disc space between opposed vertebral endplates, comprising:
  i) a disc spacer spreader comprising a distal pedal having lateral surfaces, the pedal adapted to enter a disc space and distract the disc space upon rotation,
  ii) a torque gauge adapted to engage the disc space spreader and report a torque produced by rotation of the spreader,
b) advancing the distal pedal into the disc space,
c) rotating the pedal to bear the lateral surfaces against the opposed endplates, and
d) reading a report of torque on the torque gauge.

DETAILED DESCRIPTION OF THE INVENTION

For the purposes of the present invention, the term "supporting structures" refers to the ligaments and portions of the annulus fibrosus surrounding the disc space that experience tension when an inplant is inserted into the disc space. The term "disc space" refers to the space between opposing intervertebral bodies when at least a portion of the nucleus pulposus has been removed.

Figure 1A:
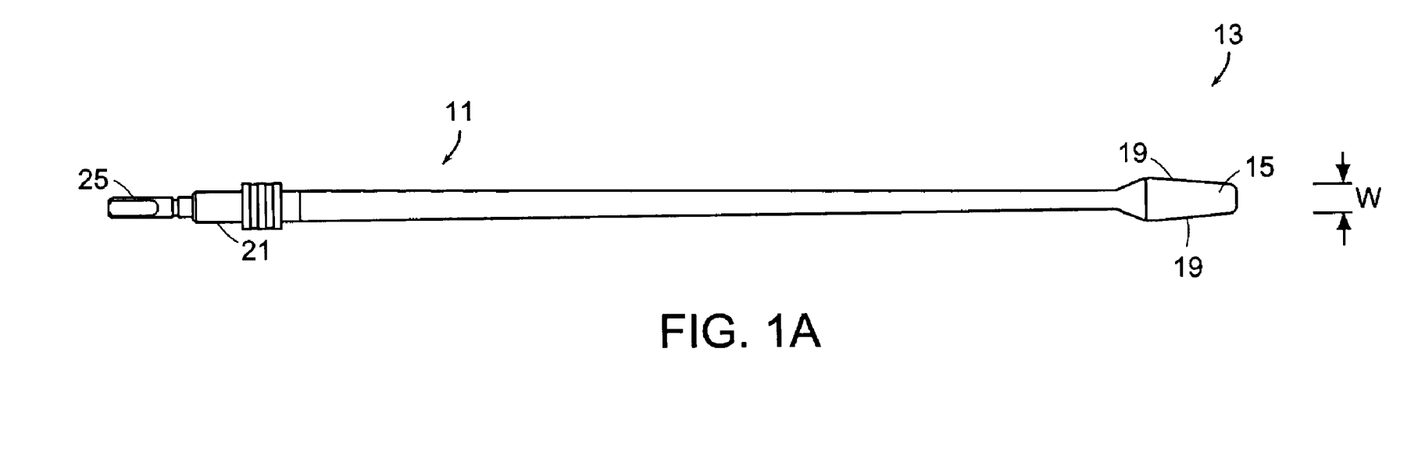
FIG. 1A discloses a top view of a preferred spreader component of an embodiment of the present invention.
Figure 1B:
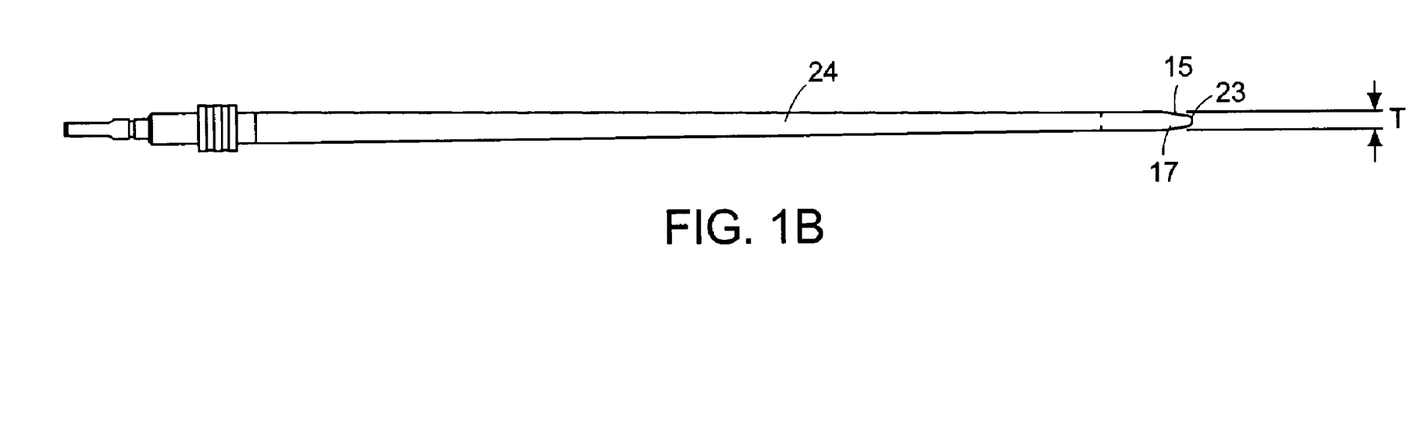
FIG. 1B discloses a side view of the distal pedal of a preferred spreader component of an embodiment of the present invention.
Figure 3:
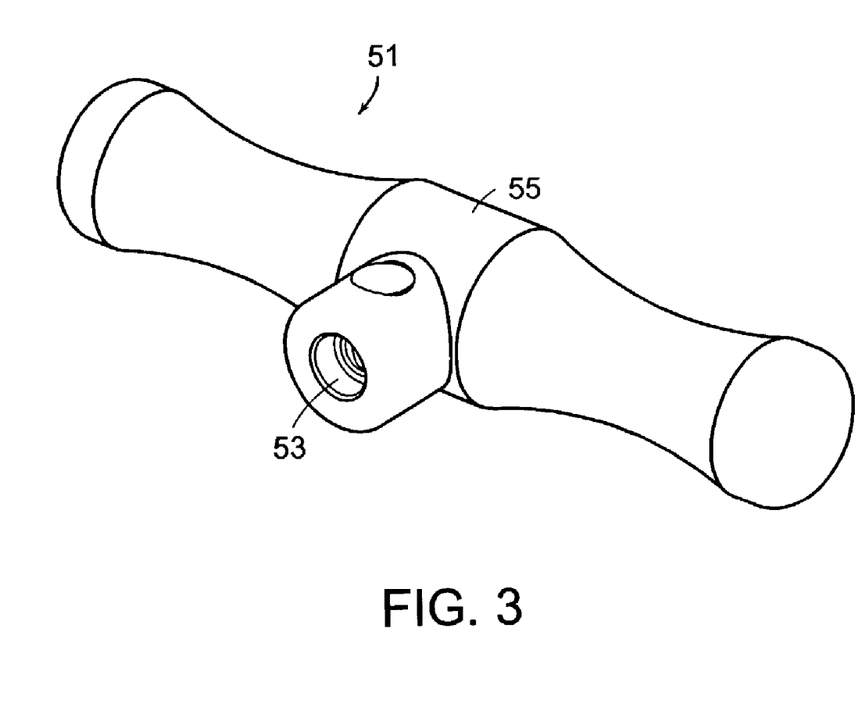
FIG. 3 discloses a perspective view of a preferred handle component of an embodiment of the present invention.

Now referring to FIGS. 1–4, there is provided an exploded view of a tensiometer 1 for measuring tension in an intervertebral disc space between opposed vertebral surfaces, comprising:
a) a disc space spreader 11 comprising:

i) a distal pedal portion 13 having upper 15 and lower 17 surfaces defining a thickness T therebetween, and lateral surfaces 19 defining a width W therebetween, the upper and lower surfaces being adapted to enter the disc space, the lateral surfaces being adapted for bearing against the opposed vertebral surfaces, the width being greater than the thickness, and ii) a proximal portion 21, and b) a torque gauge 31 comprising:

i) a housing 47 comprising a body portion 33 having:

a distal end portion 35 having an attachment port 40, and a proximal end portion 32 having a flange 38 extending radially therefrom forming a proximal face 39, ii) an intermediate twistable longitudinal beam 34 having a longitudinal axis, and comprising a distal end portion 42 fixed to the distal end portion of the body portion and a proximal end portion 36 capable of twisting rotation in response to proximally-applied axial torque, iii) a flat plate 45 attached to the proximal face of the flange, the plate having a proximal face 46 having a graduated scale 41 thereon, iv) an indicator 37 extending outwardly from the proximal end portion of the beam and adapted to rotate in correspondence with rotational movement of the longitudinal beam, the indicator being located proximal to the graduated scale, and c) a handle 51 comprising:

i) a distal portion 53 adapted for engaging the proximal portion of the beam, and ii) a proximal portion 55 adapted for gripping.

Figure 4A:
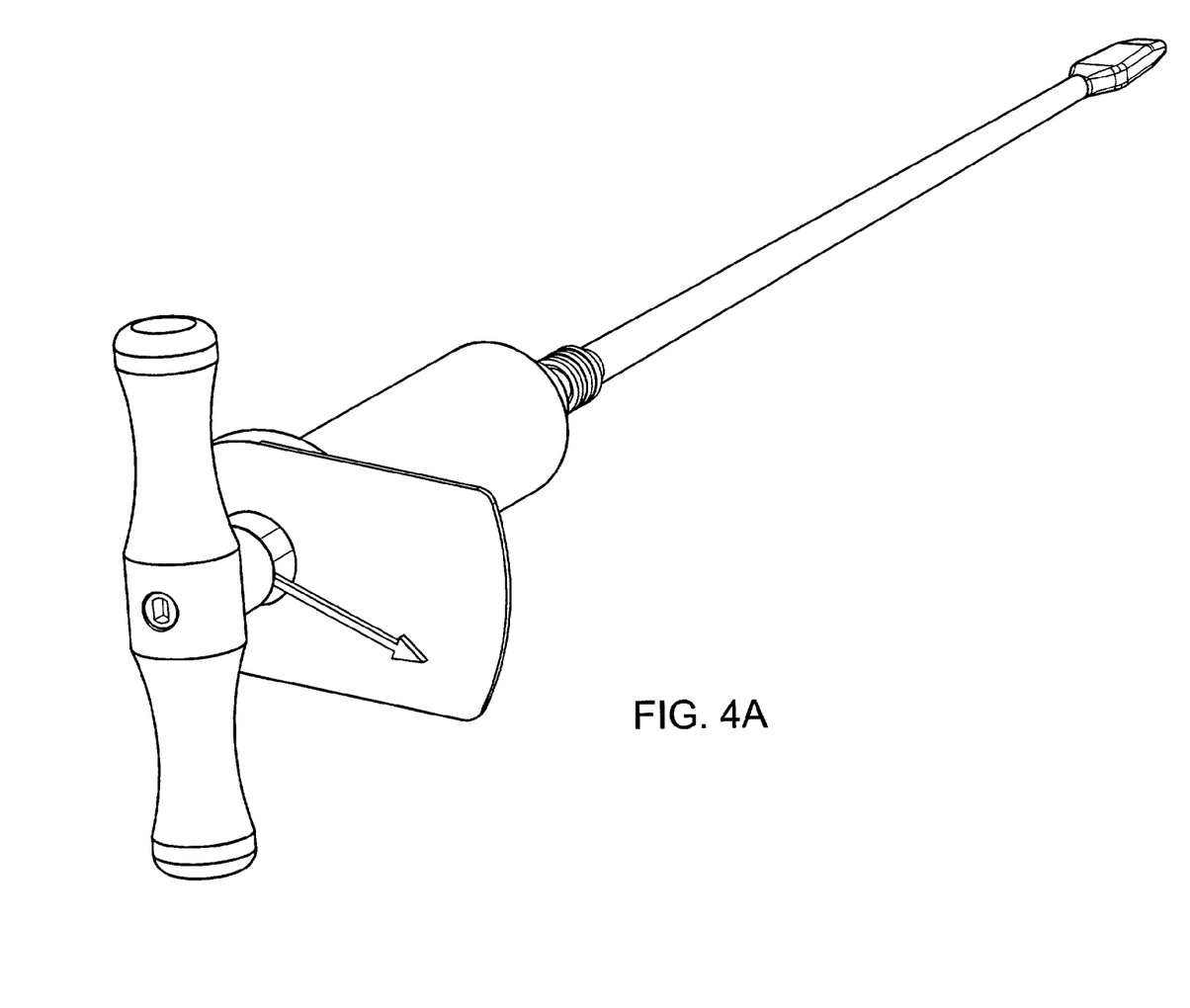
FIG. 4A discloses a perspective view of an assembled preferred embodiment of the present invention.
Figure 4B:
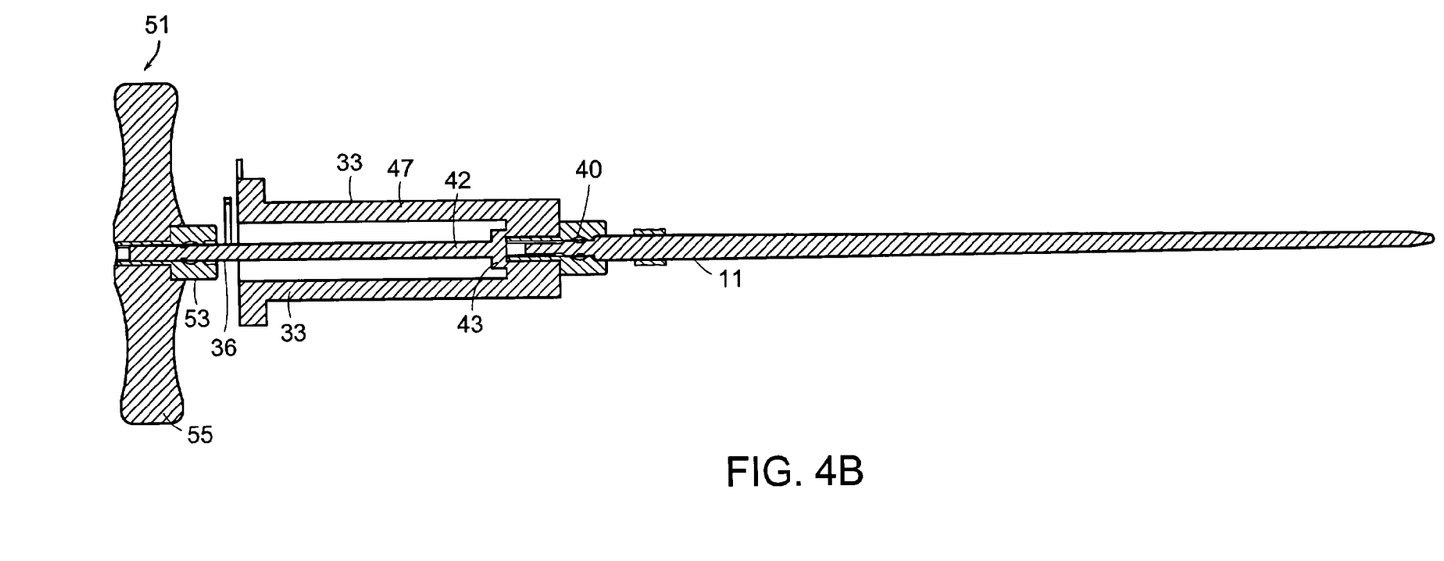
FIG. 4B discloses a cross-sectional view of FIG. 4A.

To assemble the device of FIG. 4, the proximal portion of the spreader is engaged to the distal end portion of the torque gauge, and the proximal end of the torque gauge is engaged to the distal of the handle. Any conventional engagement means can be used to achieve the spreader-torque gauge and torque gauge-handle connections.

In this particular embodiment, the proximal end of the spreader is a male connection having a radial groove, while the distal end of the torque gauge is a female connection having radial ridge and a push button feature to actuate the ridge for quickly releasing the spreader. Also in this particular embodiment, the proximal end of the torque gauge is a male connection having a radial groove, while the distal end of the handle is a female connection having a radial ridge and a push button feature for quickly releasing the spreader. In other embodiments, the male-female connection features of either the distal junction, the proximal junction or both are reversed.

The aim of the device of the first embodiment is to measure the tension within the disc space provided by the supporting structures produced in response to the force produced by rotation of the pedal and the consequent distraction of the disc space. This is accomplished by measuring the torque recorded by the torque gauge in response to rotation of the pedal that achieves maximal distraction. In addition, the device of the first embodiment also allows the surgeon to determine the size of the implant.

In preferred embodiments, the distal end portion of the longitudinal beam is fixedly connected to the distal end portion of the body portion of the housing, while the proximal end portion of the longitudinal beam is fixedly connected to the distal portion of the handle. When the handle is rotated, the torque transmitted through the handle causes the beam to deflect relative to the housing. The extent of this deflection is quantified by the movement of the indicator in relation to the graduated scale of the body portion.

The range of appropriate levels of tension suitable for the implantation of an intervertebral implant is typically well known. Therefore, the surgeon typically desires to select a size of implant that allows its insertion into the disc space to produce a tension upon the supporting structures within the desired range.

Knowledge of this proper level of tension further allows a determination of the corresponding torque required to provide complete distraction by a given spreader. The correspondence between the level of tension in a distracted disc space and the maximum torque required to rotate a given spreader to produce that distraction can be determined through experimentation. For example, it is believed that, in some instances, the torque required to sufficiently distract the disc space is between 30 lb.-in. and 120 lb.-in. Therefore, once the torque for a given spreader of a known height is obtained by the surgeon, the corresponding tension within the disc space can be easily calculated. Typically, the surgeon begins with small spreaders whose distraction require relatively low torques and produce correspondingly low tensions. The surgeon then repeats the procedure with larger and larger spreaders until the maximum torque registered for a given spreader is within the range of torques corresponding to the desired level of disc space tension. The spreader height corresponding to the most appropriate tension is then identified, and an implant of approximately that height is selected.

The disc space spreader can be any device adapted to distract a disc space by entering the disc space and rotating its distal end. Examples of such spreaders are well known in the art. In general, the spreader is designed to efficiently transmit any torque generated by the handle to rotate the pedal walls and achieve distraction.

The spreader comprises a distal pedal 13 having a thickness T predetermined to easily enter the disc space and a width W predetermined to distract the disc space upon a 90 degree rotation of the inserted pedal. Preferably, the width defined by the lateral surfaces of the pedal is between 2 and 4 times the thickness T defined by the upper and lower surfaces of the pedal. In this condition, the thickness may be sufficiently small so as to enter even a significantly collapsed disc space. More preferably, the width W is between 6 mm and 20 mm. In this condition, the pedal is sized to easily enter most disc spaces and provide full distraction upon rotation.

It has been found that sharp junctions between the pedal surfaces may cause damage to the opposed endplates. Therefore, in some embodiments, the lateral surfaces have a convex shape. In some embodiments, at least one of the lateral surfaces and the upper surface meet at a junction having a radius, preferably of between 0.5 mm and 1.5 mm. The provision of a convex shaped lateral surface and/or a radiused junction provides a smoother contact with the endplates during rotation of the spreader.

It has been found that, in situations in which the disc space is significantly collapsed, sharp leading edges on the pedal may damage the endplates. Therefore, in some embodiments, it has been found providing a taper 23 upon the leading edge of the pedal allow the pedal to more easily enter the disc space. In some embodiments, the taper is a radius.

In some embodiments, the proximal portion of the pedal comprises a radially-extending stop, which is designed to abut the front wall of at least one of the opposing vertebral bodies and prevents the surgeon from proceeding too far into the disc space.

Because it is contemplated that the device of the present invention will be used in procedures using an anterior approach, it may be useful to provide a relatively long spreader so that the measuring means need not enter the patient's body cavity. Therefore, in some embodiments, spreader has an intermediate portion 24 having a length that is sized to provide a device working length of about 200 mm. In some embodiments, the intermediate portion of the spreader has a length whereby the proximal end of the spreader is outside of the patient's body cavity.

The proximal portion of the spreader is preferably adapted to engage the distal portion of the torque gauge. In some embodiments, the proximal portion comprises a male connector portion 25 adapted to be inserted into a female connector portion disposed on the torque gauge.

Preferably, the torque gauge of the present invention is a device capable of receiving a torque and recording that torque on a readable display. For example, the torque gauge can be a mechanically-based torque gauge or an electrically-based torque gauge.

Preferably, the torque gauge comprises:
a) a housing,
b) a twistable longitudinal beam having a distal end fixedly attached to the housing and a proximal end (preferably, fixedly attached to a handle), and
c) a means 48 for measuring a deflection of the beam relative to the housing when a torque is applied to the beam.

In some embodiments, the housing comprises a body fixedly attached to the distal portion of the beam. In some embodiments, this body forms an outer shell around the beam. In some embodiments, the body further includes a flange 38 extending outwardly from the body and forming a proximal face 39. Preferably, this flange is located on the proximal portion of the outer shell.

In some embodiments (not shown), the housing comprises a body fixedly attached to the spreader, preferably the proximal portion of the spreader. In some embodiments, this body forms an outer shell around the proximal portion of the spreader. In some embodiments, the body further includes a flange extending outwardly from the body and forming a proximal face. Preferably, this flange is located on the proximal portion of the outer shell.

Generally, the twistable beam is designed so that the proximal end can twist about the longitudinal axis in relation to the distal end when a torque is applied to the proximal end. Preferably, the twistable beam has a rectangular cross-section, and has a length that is at least 10 times its greatest cross-sectional dimension. In some embodiments, the distal end of the beam comprises an attachment flange 43 shaped to attach to the housing.

Generally, the means for measuring the deflection of the beam comprises a stationary member fixedly connected to the housing, and a moveable member fixedly connected to the beam. This means provides a visual display of the torque measurement.

Preferably, the stationary member comprises a flat plate 45 disposed proximal to the housing flange 38. Preferably, the flat plate 45 is attached to the proximal face of the flange. Preferably, the plate has a proximal face 46 having a graduated scale 41 thereon at a radius. Preferably, the plate is removably attached to the flange. Preferably, the graduated scale provides gradations of torque.

In some embodiments, the graduated scale is provided directly upon the proximal face of the flange.

Figure 2A:
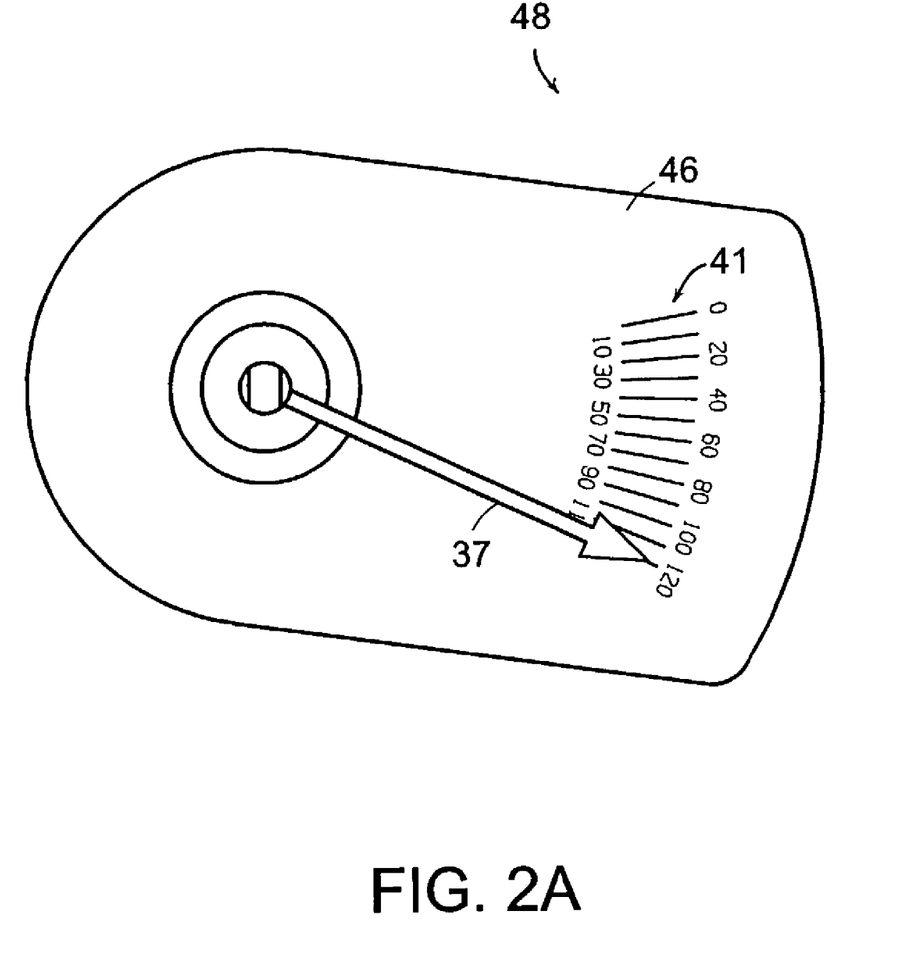
FIGS. 2A–D disclose proximal, first side, second side, and distal views of a preferred torque gauge component of an embodiment of the present invention.
Figure 2B:
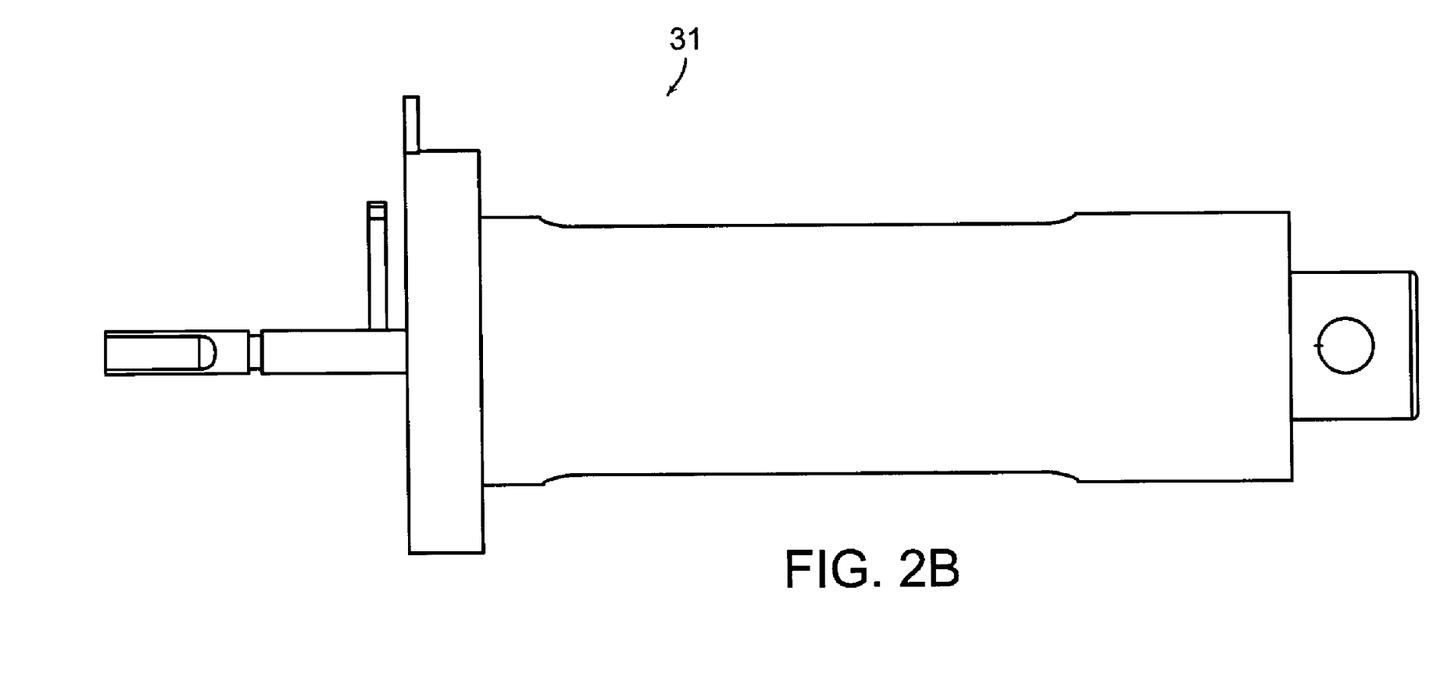
Figure 2C:
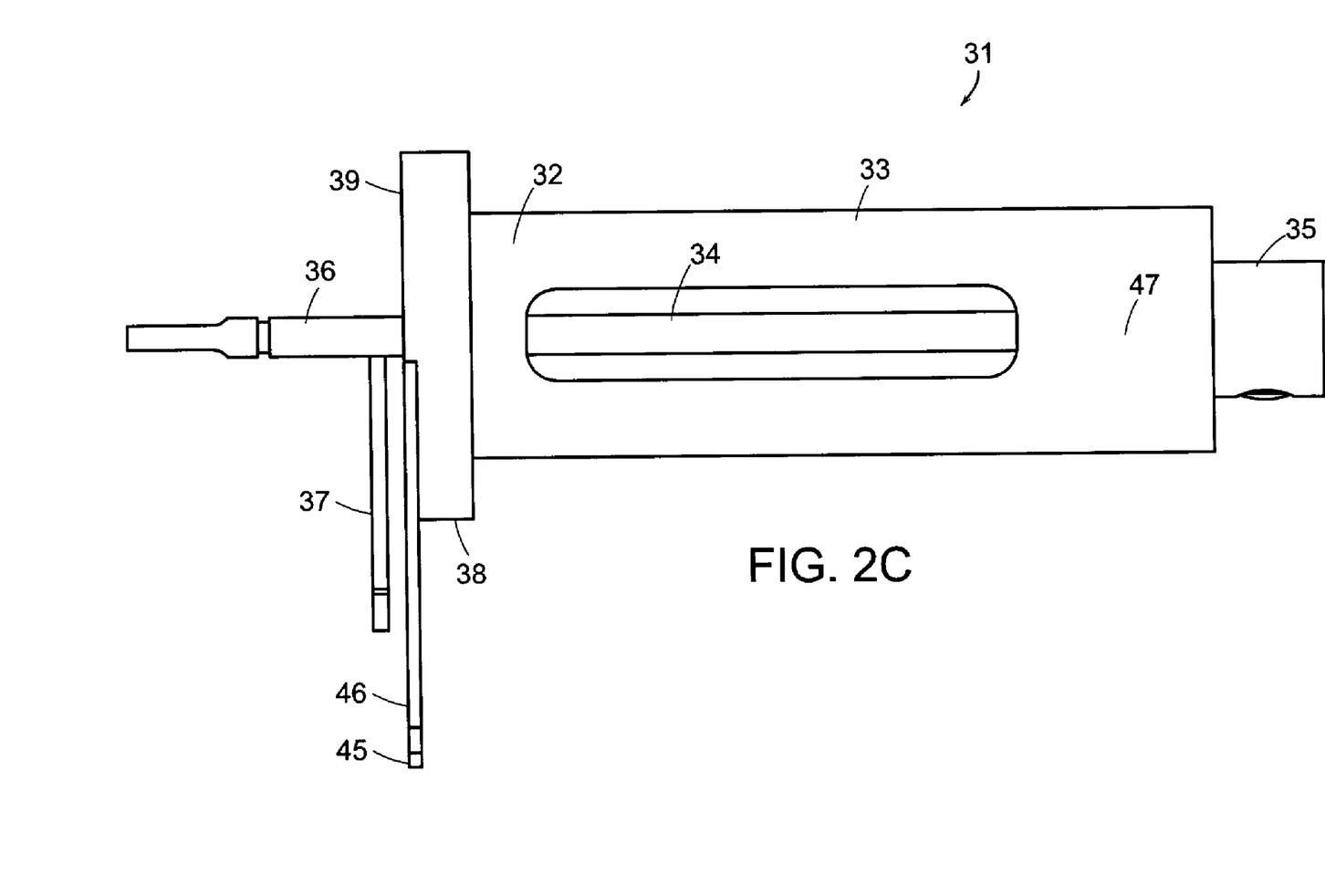
Figure 2D:
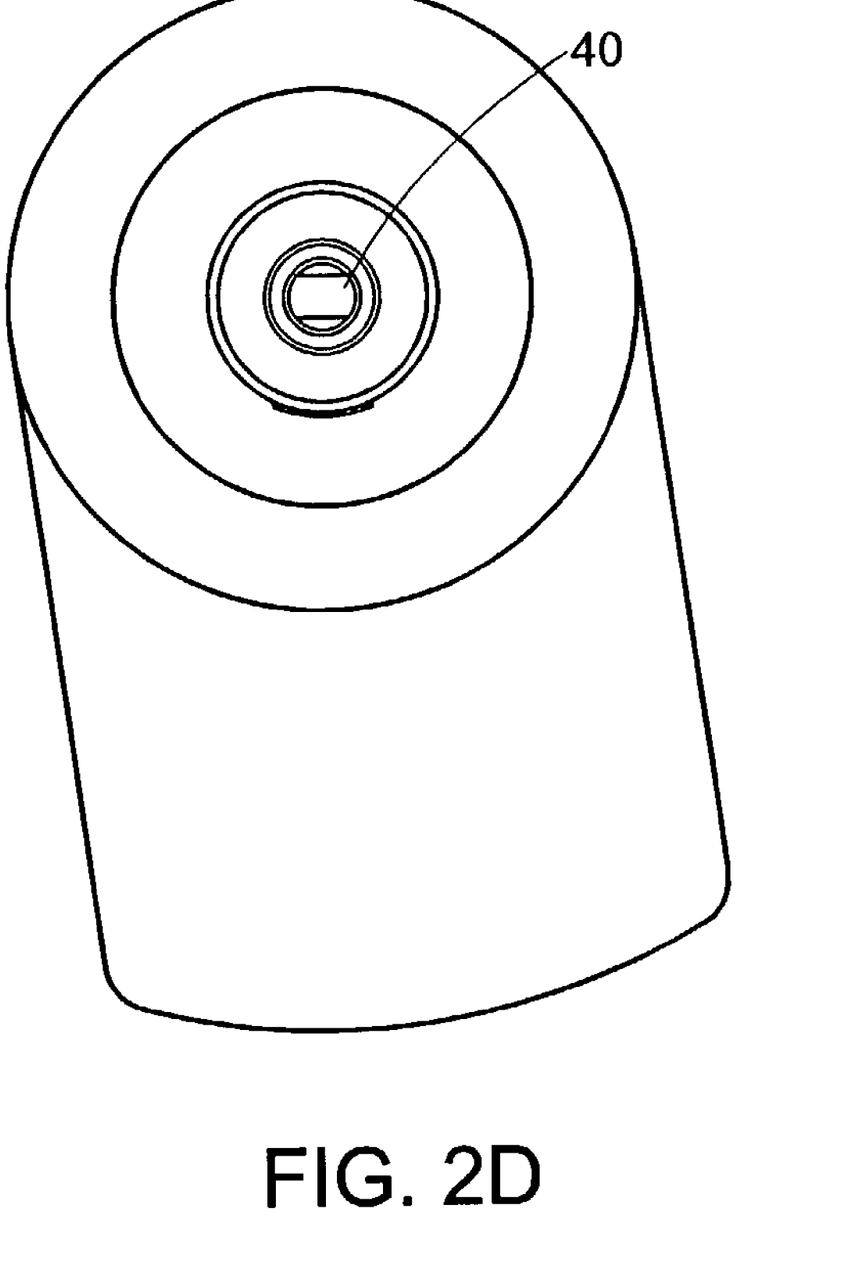

In some embodiments, the moveable member is attached to the beam, preferably the proximal portion of the beam, and extends radially outward from the beam. In some embodiments, the moveable member is attached to the handle, and extends radially outward from the handle. In some embodiments, the moveable member comprises a needle 37 extending radially outward from either the beam or handle, more preferably the beam. In some embodiment the moveable member has a needle shape extending radially to the radius of the graduated scale.

In some embodiments, the moveable member is located at a position proximal to the stationary member. In this condition, the surgeon can easily read the location of the moveable member upon the background scale of the stationary member.

In preferred embodiments, the means for measuring the deflection comprises a distal graduated scale located on the stationary member, and a proximal indicator located on the moveable member (as in FIG. 2*a*). However, in other embodiments, the means for measuring the deflection comprises a proximal graduated scale located on the stationary member, and a distal indicator located on the moveable member.

In some embodiments, the torque gauge is a reaction torque transducer, preferably marketed by Interface, Inc of Scottsdale, Ariz. In other embodiments, the torque gauge comprises an axial deflection beam, marketed by Beere Precision Medical Instruments, Inc. of Kenosha, Wis. 53144.

In some embodiments, the device of the present invention further comprises a proximal handle adapted for connection to the proximal end portion of the torque gauge. This handle can be easily grasped and rotated to produce rotation of the device, including rotation of the distal portion of the spreader.

The distal portion of the handle is preferably adapted to engage the proximal end portion of the torque gauge. In some embodiments, the distal portion of the handle comprises a female connector portion adapted to receive a male connector portion disposed on the proximal portion of the torque gauge.

The proximal portion of the handle preferably comprises two laterally extending arms adapted to be grasped together by a single hand of the surgeon and rotated about 180 degrees in one turn. Preferably, these arms have a gross concave shape for ease of grasping.

Typically, the spreader, torque gauge and handle components of the present invention can be made out of any material commonly used in medical instruments. If the device is designed to be reusable, then it is preferred that all the components be made of stainless steel. If the device is designed to be disposable, then it is preferred that some of the components be made of plastic. Preferably, at least one component is sterilized. More preferably, each component is sterilized.

Preferably, the device of the present invention is used to measure the tension in an intervertebral disc space. In some embodiments, the disc space comprises opposing unprepared vertebral endplates. In some embodiments, the disc space comprises opposing vertebral endplates that have been prepared by a milling means. In some embodiments, the disc space includes at least a portion of an annulus fibrosus retained from the intervertebral disc. In other embodiments, both the nucleus pulposus and the annulus fibrosus have been removed. In some embodiments, the disk space has a height that is between 10% and 40% of the height of a healthy disc. In some embodiments, the disk space has a height that is between 40% and 60% of the height of a healthy disc. In some embodiments, the disk space has a height that is between 60% and 80% of the height of a healthy disc.

This prophetic example describes the operation and use of the spreader embodiment of the present invention.

First, the surgeon removes at least a portion of a patient's intervertebral disc to create an intervertebral disc space.

Second, the surgeon orients the distal pedal portion of the spreader so that the upper and lower surfaces thereof face the respective lower wall of the upper vertebral body and the upper surfaces of the lower vertebral body.

Third, the surgeon inserts the oriented pedal into the disc space, stopping at a predetermined distance such as 30 mm, and before the distal end of the spreader reaches the distal end of the disc space.

Fourth, the surgeon rotates the pedal about an arc slightly less than 90 degrees so that the lateral surfaces of the spreader bear against the endplates and distract the disc space.

Fifth, the surgeon reads the maximum torque displayed by the indicator on graduated plate during the distraction.

Sixth, the surgeon determines whether the maximum torque is within the range of desirable torque.

If the surgeon determines that the maximum torque is not within the desired range, then the surgeon selects a larger or smaller spreader and repeats steps 2–6 above.

If the surgeon determines that the displayed torque is within the desired range, then the surgeon selects an implant whose size corresponds to the width of the pedal of the spreader.

Eighth, the surgeon implants the selected implant.

I claim:

1. A tensiometer for measuring tension in an intervertebral disc space between opposed vertebral surfaces, comprising:
    a) a disc space spreader adapted to enter a disc space and distract the disc space upon rotation, wherein the spreader comprises:
        i) a distal pedal portion having upper and lower surfaces defining a thickness T therebetween, and lateral surfaces defining a width W therebetween, the upper and lower surfaces being adapted to enter the disc space, the lateral surfaces being adapted for bearing against the opposed vertebral surfaces, the width being greater than the thickness, wherein the lateral surfaces have a convex shape, and
        ii) a proximal portion, and
    b) a torque gauge adapted to engage the disc space spreader and report a torque required for the rotation of the spreader.

2. The tensiometer of claim 1 wherein the width defined by the lateral surfaces of the pedal is between 2 and 4 times the thickness defined by the upper and lower surfaces of the pedal.

3. The tensiometer of claim 2 wherein the width of the pedal is between 6 mm and 20 mm.

4. The tensiometer of claim 1 wherein at least one of the lateral surfaces and the upper surface meet at a junction, wherein the junction has a radius of between 0.5 and 1.5 mm.

5. The tensiometer of claim 1 wherein the pedal portion further comprises a tapered leading edge.

6. The tensiometer of claim 1 wherein the spreader further comprises an intermediate portion sized to provide a device working length of about 200 mm.

7. The tensiometer of claim 1 wherein the proximal portion of the spreader is adapted to engage a distal portion of the torque gauge.

8. The tensiometer of claim 1 wherein the proximal portion of the pedal portion comprises a radially-extending stop.

9. The tensiometer of claim 1 wherein the torque gauge comprises:
    i) a housing,
    ii) a twistable longitudinal beam having a distal end fixedly attached to the housing and a proximal end, and
    iii) a means for measuring a deflection of the beam relative to the housing when a torque is applied to the beam.

10. The tensiometer of claim 9 wherein the beam has a shape adapted to twist about the longitudinal axis in relation to the distal end when a torque is applied to the proximal end.

11. The tensiometer of claim 9 wherein the beam has a length and a greatest cross-sectional dimension and the length is at least 10 times greater than the greatest cross-sectional dimension.

12. The tensiometer of claim 9 wherein the distal end of the beam comprises an attachment flange.

13. The tensiometer of claim 9 wherein the housing comprises a body fixedly attached to the distal portion of the beam.

14. The tensiometer of claim 13 wherein the body forms an outer shell around the beam.

15. The tensiometer of claim 13 wherein the body further includes a flange extending outwardly from the body and forming a proximal face.

16. The tensiometer of claim 15 wherein the flange is located on a proximal portion of an outer shell.

17. The tensiometer of claim 12 wherein the housing comprises a body fixedly attached to the spreader.

18. The tensiometer of claim 17 wherein the body is fixedly attached to a proximal portion of the spreader.

19. The tensiometer of claim 18 wherein the body forms an outer shell around a proximal portion of the spreader.

20. The tensiometer of claim 17 wherein the body further includes a flange extending outwardly from the body and forming a proximal face.

21. The tensiometer of claim 20 wherein the flange is located on a proximal portion of an outer shell.

22. The tensiometer of claim 9 wherein the means for measuring the deflection of the beam comprises a stationary member fixedly connected to the housing, and a moveable member fixedly connected to the beam.

23. The tensiometer of claim 22 wherein the stationary member comprises a plate having a proximal face having a graduated scale thereon at a radius.

24. The tensiometer of claim 23 wherein the moveable member has a needle shape extending radially to the radius of the graduated scale.

25. The tensiometer of claim 24 wherein the moveable member is attached to a proximal portion of the beam.

26. The tensiometer of claim 22 further comprising:
    c) a handle comprising:
        i) a distal portion adapted for engaging a proximal portion of the beam, and
        ii) a proximal portion adapted for gripping.

27. The tensiometer of claim 26 wherein the moveable member is located on the handle, and extends radially outward from the handle.

28. The tensiometer of claim 22 wherein the moveable member is located at a position proximal to the stationary member.

29. The tensiometer of claim 22 wherein the stationary member comprises a graduated scale, and the moveable member comprises an indicator.

30. The tensiometer of claim 1 wherein the torque gauge comprises:
  i) a body portion having:
    a distal end portion having an attachment port, and
    a proximal end portion having a flange extending radially therefrom forming a proximal face,
  ii) an intermediate twistable longitudinal beam having a longitudinal axis, and comprising a distal end portion fixed to the distal end portion of the body portion and a proximal end portion capable of twisting rotation in response to proximally-applied axial torque,
  iii) a flat plate attached to the proximal face of the flange, the plate having a proximal face having a graduated scale thereon, and
  iv) an indicator extending outwardly from the proximal end portion of a bar and adapted to rotate in correspondence with rotational movement of the longitudinal beam, the indicator being located proximal to the graduated scale.

31. A method of measuring tension in an intervertebral disc space formed from opposed vertebral endplates, comprising:
  a) providing a tensiometer for measuring tension in an intervertebral disc space between opposed vertebral endplates, comprising:
    a disc space spreader comprising a distal pedal having lateral surfaces, the pedal adapted to enter a disc space and distract the disc space upon rotation,
    a torque gauge adapted to engage the disc space spreader and report a torque produced by rotation of the spreader,
  b) advancing the distal pedal into the disc space,
  c) rotating the pedal to bear the lateral surfaces against the opposed endplates, and
  a) reading a report of torque on the torque gauge.

* * * * *